United States Patent [19]

Inglett

[11] Patent Number: 5,266,467
[45] Date of Patent: Nov. 30, 1993

[54] ENZYMATIC PRODUCTION OF MALTOHEXAOSE-RICH COMPOSITIONS

[75] Inventor: George E. Inglett, Peoria, Ill.

[73] Assignee: The United States of America as represented by the Secretary of Agriculture, Washington, D.C.

[21] Appl. No.: 649,348

[22] Filed: Feb. 1, 1991

Related U.S. Application Data

[63] Continuation of Ser. No. 189,093, May 2, 1988, abandoned.

[51] Int. Cl.$^5$ ............................................. C12P 19/22
[52] U.S. Cl. ..................................... 435/99; 435/832
[58] Field of Search ................................. 435/99, 832

[56] References Cited

U.S. PATENT DOCUMENTS

| | | | |
|---|---|---|---|
| 4,241,183 | 12/1980 | Witt et al. | 435/99 X |
| 4,284,722 | 8/1981 | Tamuri et al. | 435/94 |
| 4,298,400 | 11/1981 | Armbruster et al. | 435/99 X |
| 4,493,893 | 1/1985 | Mielenz et al. | 435/172.3 |
| 4,603,110 | 7/1986 | Morehouse et al. | 435/96 |

FOREIGN PATENT DOCUMENTS

| | | | |
|---|---|---|---|
| 189838 | 8/1986 | European Pat. Off. | 435/99 |
| 252730 | 1/1988 | European Pat. Off. | 435/99 |

OTHER PUBLICATIONS

John Robyt et al., "Action Pattern and Specificity of an Amylase from *Bacillus subtilis*," Arch. Biochem. Biophys. 100: 451–460 (1963) [note: only 451–460 furnished].

L. Slomin'ska et al., "Studies on the Application of Maltogenic Amylase in the Production of Maltose Containing Syrup," Starch/Starke 38(6): 205–210 (1986).

H. Outtrup et al., "Properties and Application of a Thermostable Maltogenic Amylase Produced by a Strain of Bacillus Modified by Recombinant-DNA Techniques," Starch/Starke 36(12): 405–411 (1984).

G. E. Inglett, "Action Pattern of *Bacillus licheniformis* Alpha-Amylase on Ordinary, Waxy and High-Amylose Corn Starches and Their Hydroxypropyl Derivatives," J. Food Biochem. 11: 249–258 (1987) (NRRC #5886).

Teruo Nakakuki et al., "Action Patterns of Various Exo-Amylases and the Anomeric Configurations of Their Products," Carbohyd. Res. 128: 297–310 (1984).

*Primary Examiner*—Glennon H. Hollrah
*Assistant Examiner*—Shailendra Kumar
*Attorney, Agent, or Firm*—M. Howard Silverstein; John D. Fado; Curtis P. Ribando

[57] ABSTRACT

Malto-oligosaccharide compositions which contain up to about 40% maltohexaose by weight are produced from starchy substrates and maltodextrins by a simple, one-step hydrolysis with certain thermostable α-amylase from *Bacillus stearothermophilus*. This process is particularly useful in the production of novel compositions with properties that will lead to new applications in both food and nonfood industries.

5 Claims, No Drawings

ENZYMATIC PRODUCTION OF MALTOHEXAOSE-RICH COMPOSITIONS

This application is a continuation of application Ser. No. 07/189,093, filed May 2, 1988, now abandoned.

BACKGROUND OF THE INVENTION

1. Field of the Invention

Malto-oligosaccharides, also referred to as maltodextrins and dextrose syrup solids, are produced from starch by hydrolysis with α-amylases. These carbohydrates are used in adhesives and in food applications such as syrups, flavor encapsulation, texture control, binding agents, carriers for low-calorie sweeteners, and gels in reduced-calorie foods. This invention relates to the production of novel malto-oligosaccharide compositions that contain a large proportion of maltohexaose.

2. Description of the Prior Art

Thermally stable α-amylases have enabled a rapid advance in the commercial production of malto-oligosaccharides by enzymatic hydrolysis of starch. However, the mode of the amylase action on starches in only partly understood because the fine structure of starches is still obscure. Furthermore, amylases from different sources behave differently, and their action patterns are dependent on reaction conditions. Certain amylases are now known to yield distinctive patterns of malto-oligosaccharide products that are at variance with the distribution of products that would be predicted on the basis of random cleavage of starch molecules. Robyt et al. [Arch. Biochem. Biophys. 100: 451–467 (1963)] teach that α-amylase from *Bacillus subtilis* selectively forms maltotriose and maltohexaose. Nakakuki et al. [Carbohydr. Res. 128: 297–310 (1984)] report that the α-amylase from *B. licheniformis* degrades short-chain amylose at 1% concentration and 40° C. to give mainly maltopentaose and maltotriose with slightly smaller quantities of maltose. In contrast, Inglett [J. Food Biochem. 11: 249–258 (1987)] shows that this same enzyme, acting on higher substrate concentrations (20–30% starch) and at a higher temperature (95° C.), yields increased quantities of maltose, essentially equivalent to or slightly higher than the other two oligomers. Slomin'ska et al. [Starch/Starke 38(6): 205–210 (1986)] show that a 72-hr saccharification of liquified starch with a thermostable maltogenic amylase from *B. stearothermophilus* virtually eliminates the maltohexaose (G6) constituent. Outrup et al. [Starch/Starke 36(12): 405–411 (1984) shows that treatment of amylopectin with a *B. stearothermophilus* amylase produces only traces of maltohexaose (G6).

SUMMARY OF THE INVENTION

I have now surprisingly found that certain thermostable α-amylases have a unique and unexpected action on starches and maltodextrins to produce large quantities of maltohexaose [degree of polymerization (DP) 6], with comparatively minor amounts of oligomeric constituents of DP greater than 6. These amylases have utility in a process for converting starch into products with potentially unique and expanded markets.

In accordance with this discovery, it is an object of the invention to provide a simple, one-step method for converting starch into novel malto-oligosaccharide compositions that contain a large proportion of maltohexaose.

It is also an object of the invention to provide novel maltodextrins and dextrose syrup solids containing maltohexaose as the dominant oligomer and with properties leading to potential new uses.

Other objects and advantages of the invention will become readily apparent from the ensuing description.

DETAILED DESCRIPTION OF THE INVENTION

Suitable starting materials contemplated for use in the invention include unmodified natural granular starches such as regular cereal, potato, and tapioca starch, as well as waxy starches and high-amylose starches. These materials are prepared for enzyme treatment by gelatinization. For purposes of this invention, gelatinization is accomplished preferably by passage of an aqueous slurry of the starch through a steam-injection cooker at a temperature of about 120°–165° C. to ensure thorough dispersion of the starch. Other methods of gelatinization are well-known in the art. Alternatively, pregelatinized starch and maltodextrins would serve as useful starting materials. The concentration of substrate should be in the range of about 5–45% by weight.

A suitable calcium salt is added to the aqueous dispersion of substrate in an amount sufficient to stabilize the subsequently added α-amylase (preferably about 50 ppm of calcium). The pH of the resulting starchy dispersion is adjusted to about 6.0 with sodium hydroxide or other alkali, and the dispersion is treated at a temperature in the range of 70°–100° C., preferably about 95° C., with a thermostable α-amylase.

The thermostable α-amylases useful herein are those referred to as 1,4-alpha-D-glucan glucanohydrolases and having the essential enzymatic characteristics of those produced by the *B. stearothermophilus* strains ATCC Nos. 31,195; 31,196; 31,197; 31,198; 31,199; and 31,783. These strains are described in U.S. Pat. No. 4,284,722, which is herein incorporated by reference. Other sources of this enzyme include organisms such as *B. subtilis* which have been genetically modified to express the thermostable α-amylase of *B. stearothermophilus* as described in U.S. Pat. No. 4,493,893, herein incorporated by reference. These enzymes are available commercially under the name "Enzeco Thermolase" (Enzyme Development, Div., Biddle Sawyer Corp., New York, N.Y.).

The level of enzyme suitable for use in this process is generally in the range of about 3–25 units per g of starch or dextrin, where 1 unit of bacterial α-amylase activity is the amount of enzyme required to hydrolyze 10 mg of starch per minute under specified conditions [Enzyme Development, Div., Biddle Sawyer Corp., New York, N.Y., Technical Bulletin No. 20 (Revised 7/86)]. Similarly, the duration of treatment depends on the product desired and will generally range from about 10–60 min; with 30–50 min being preferred for enzyme concentrations in the range of 10–20 units/g substrate; and 10–30 min being preferred for enzyme concentrations in the range of 20–25 units/g substrate.

After the desired conversion time, it is preferable to decolorize the resulting mixture with activated carbon and add a filter aid to facilitate subsequent recovery of the hydrolyzate. The pH is then adjusted to 3.5–4.0, such as with 0.2N sulfuric acid, and the product is heated at about 95° C. for 10 min to inactivate remaining enzyme. The pH is then adjusted to about 6.5, such as with 1N sodium hydroxide and the product is separated by filtration and then dried by any of a variety of techniques as within the skill of the person in the art.

The products of this invention differ from commercially available maltodextrins and dextrose syrup solids in that the latter products contain a fairly uniform distribution of oligosaccharides with no preponderance of any particular oligomer. It is therefore envisioned that the maltohexaose-rich products of this invention will have unique properties that will lead to new food applications in fields such as flavor encapsulation, texture control, and binding agents, as well as new industrial applications. These products might also serve as starting materials in new procedures for preparing carbohydrate compositions such as cyclodextrins.

The following examples are presented only to further illustrate the invention and are not intended to limit the scope of the invention which is defined by the claims.

All percentages herein disclosed are by weight unless otherwise specified.

EXAMPLE 1

Standard Process Conditions

Two hundred g (dry basis) of high-amylose corn starch ("Amylomaize VII," American Maize-Products Co., Hammond, Ind.) was slurried in 800 ml of water containing 50 ppm of calcium (0.185 g/l $CaCl_2.2H_2O$) and passed through a steam-injection cooker at 138°–143° C. (30–40 psi of steam pressure). The gelatinized starch paste was collected in a Dewar flask, and the pH was adjusted to 6.0 with 1.0N sodium hydroxide. Thermostable α-amylase ("Enzeco Thermolase," supra) was added to the starch paste at 95° C. in an amount sufficient to provide 16.5 units (supra) per g of starch. Samples of converted starch were removed 20, 40, and 60 min after addition of the enzyme. To each sample was added, with stirring, activated carbon ("Darco G-60," E M Science, Div., E M Industries, Inc., Cherry Hill, N.J.) sufficient to provide a concentration of 0.1%, and filter aid ("Hyflo Filter Cel," Manville, Fitration & Minerals Div., Denver, Colo.) sufficient to provide a concentration of 2%. The pH was adjusted to 3.5–4.0 with 0.2N sulfuric acid, and the products were heated at 95° for 10 min to inactivate remaining enzyme. The pH was then raised to 6.5 with 1N sodium hydroxide, and the mixtures were filtered hot through a bed of filter aid (supra) on filter paper ("Whatman No. 1," Whatman Chemical Separation Inc., Clifton, N.J.) on a Buchner funnel under vacuum. The filtrates were spray-dried (Pulvis Mini Spray Dryer, Model GA-31, Yamato, Northbrook, Ill.), and the carbohydrate composition of the products was determined by high-pressure liquid chromatography (Inglett, supra). The analytical results in the Table, below, show that highest yields of maltohexaose were obtained with conversion times of 40 and 60 min.

EXAMPLES 2–3

Effect of Enzyme Level

Compositions were prepared as described in Example 1 except that the α-amylase level was 11.0 units per g of starch in Example 2 and 22.0 units per g in Example 3.

EXAMPLES 4–5

Effect of pH

Compositions were prepared as described in Example 1 except that the pH during enzyme conversion of the starch was 7.0 in Example 4 and 5.0 in Example 5. The results in the Table show that pH 6.0 (Example 1) is the preferred pH, but that slight variations above or below this value would not significantly affect the yield of maltohexaose.

EXAMPLE 6

Conversion of Potato Amylose

Compositions were prepared as described in Example 1 except that the starchy substrate was potato amylose (Avebe America, Inc., Hopelawn, N.J.) instead of high-amylose corn starch. The results in the Table show that yields of maltohexaose from potato amylose were slightly less than those from high-amylose corn starch (Example 1).

It is understood that the foregoing detailed description is given merely by way of illustration and that modification and variations may be made therein without departing from the spirit and scope of the invention.

TABLE

| Example | Enzyme concentration (units/g substrate) | pH | Conversion time (min) | Amount of contituent[a], wt. % | | | | | | | | | |
|---|---|---|---|---|---|---|---|---|---|---|---|---|---|
| | | | | DP >9 | DP-9 | DP-8 | DP-7 | DP-6 | DP-5 | DP-4 | DP-3 | DP-2 | DP-1 |
| 1A | 16.5 | 6 | 20 | 29.7 | 0.2 | 0.8 | 12.3 | 22.0 | 7.8 | 6.2 | 14.0 | 6.9 | 0 |
| 1B | 16.5 | 6 | 40 | 10.9 | 0 | 0.2 | 0 | 38.7 | 12.6 | 8.9 | 17.5 | 10.6 | 0.6 |
| 1C | 16.5 | 6 | 60 | 8.2 | 0 | 0.1 | 0 | 37.1 | 14.1 | 9.1 | 18.1 | 12.3 | 1.0 |
| 2A | 11.0 | 6 | 20 | 18.8 | 0.1 | 0.7 | 10.7 | 25.8 | 10.8 | 8.2 | 16.5 | 8.1 | 0.3 |
| 2B | 11.0 | 6 | 40 | 8.2 | 0 | 0 | 0 | 34.8 | 16.1 | 9.3 | 18.7 | 12.1 | 0.9 |
| 2C | 11.0 | 6 | 60 | 5.4 | 0 | 0 | 0.1 | 31.3 | 19.1 | 9.3 | 19.2 | 14.0 | 1.5 |
| 3A | 22.0 | 6 | 20 | 6.2 | 0 | 0 | 0 | 34.9 | 16.4 | 9.2 | 18.8 | 13.3 | 1.2 |
| 3B | 22.0 | 6 | 40 | 3.6 | 0 | 0.1 | 0.1 | 28.1 | 20.9 | 9.2 | 19.0 | 16.1 | 2.9 |
| 3C | 22.0 | 6 | 60 | 2.6 | 0 | 0.1 | 0.1 | 23.2 | 21.5 | 9.2 | 19.1 | 18.5 | 5.7 |
| 4A | 16.5 | 7 | 20 | 14.3 | 0 | 0.6 | 11.8 | 27.4 | 11.0 | 8.8 | 16.2 | 9.3 | 0.4 |
| 4B | 16.5 | 7 | 40 | 6.1 | 0 | 0 | 0 | 35.7 | 15.4 | 9.6 | 18.3 | 13.5 | 1.2 |
| 4C | 16.5 | 7 | 60 | 4.5 | 0 | 0 | 0 | 30.6 | 18.9 | 9.9 | 18.7 | 15.3 | 2.0 |
| 5A | 16.5 | 5 | 20 | 10.2 | 0 | 0 | 0.2 | 39.7 | 12.4 | 8.5 | 17.8 | 10.7 | 0.6 |
| 5B | 16.5 | 5 | 40 | 6.5 | 0 | 0 | 0 | 35.6 | 15.9 | 9.0 | 18.7 | 13.0 | 1.2 |
| 5C | 16.5 | 5 | 60 | 6.1 | 0 | 0 | 0 | 34.8 | 16.5 | 9.1 | 19.0 | 13.5 | 1.1 |
| 6A | 16.5 | 6 | 20 | 1.6 | 0 | 0 | 10.1 | 30.2 | 15.2 | 9.5 | 20.3 | 12.2 | 0.9 |
| 6B | 16.5 | 6 | 40 | 1.0 | 0 | 0 | 0 | 33.1 | 18.8 | 9.6 | 20.4 | 14.8 | 2.3 |
| 6C | 16.5 | 6 | 60 | 0.9 | 0 | 0 | 0 | 30.7 | 20.1 | 9.6 | 20.4 | 15.6 | 2.8 |

[a]DP = degree of polymerization of dextrose, where DP-2 is disaccharide, DP-3 is trisaccharide, etc.

I claim:

1. A method for producing a maltohexaose-rich composition from a substrate selected from the group of gelatinized starches and maltodextrins comprising treating an aqueous dispersion or solution of said substrate with about 3–25 units per gram of starch of a thermostable *B. stearothermophilus* α-amylase having the maltohexaose-producing characteristics of the thermostable α-amylases produced by *B. stearothermophilus* strains ATCC No. 31,195, 31,196, 31,197, 31,198, 31,199, and 31,783 under conditions favorable to the production of maltohexaose as the dominant oligomer whereby said maltohexaose comprises at least about 20% by weight of the composition, and recovering said maltohexaose-rich composition.

2. The method as described in claim 1 wherein said starch is selected from the group consisting of regular cereal, potato, and tapioca starches, as well as waxy and high-amylose starches.

3. The method as described in claim 1 wherein said substrate is a maltodextrin.

4. The method as described in claim 1 wherein said treatment of starch with enzyme is performed at a temperature in the range of about 70°–100° C. and for a period of about 10–60 min.

5. The method as described in claim 1 wherein the amylase is present in the amount of 10–20 units/g substrate and the period of enzyme treatment is in the range of about 30–50 min.

* * * * *